United States Patent
Chattopadhyay et al.

(10) Patent No.: US 10,957,450 B2
(45) Date of Patent: Mar. 23, 2021

(54) AUTOMATIC PREDICTION OF PATIENT LENGTH OF STAY AND DETECTION OF MEDICAL CENTER READMISSION DIAGNOSES

(71) Applicant: Intel Corporation, Santa Clara, CA (US)

(72) Inventors: Rita Chattopadhyay, Chandler, AZ (US); Kalpana A. Algotar, Chandler, AZ (US); Amith Harsha, Houston, TX (US); Ravindra V. Narkhede, Chandler, AZ (US)

(73) Assignee: Intel Corporation, Santa Clara, CA (US)

( * ) Notice: Subject to any disclaimer, the term of this patent is extended or adjusted under 35 U.S.C. 154(b) by 762 days.

(21) Appl. No.: 15/396,075

(22) Filed: Dec. 30, 2016

(65) Prior Publication Data
US 2018/0189453 A1      Jul. 5, 2018

(51) Int. Cl.
*G16H 50/20* (2018.01)
*G16H 40/20* (2018.01)
*G16H 10/60* (2018.01)
*G06N 20/00* (2019.01)

(52) U.S. Cl.
CPC ............ *G16H 50/20* (2018.01); *G06N 20/00* (2019.01); *G16H 10/60* (2018.01); *G16H 40/20* (2018.01)

(58) Field of Classification Search
CPC ........ G16H 50/20; G16H 40/20; G16H 10/60; G06N 20/00
See application file for complete search history.

(56) References Cited

U.S. PATENT DOCUMENTS

| | | |
|---|---|---|
| 2007/0150307 A1 | 6/2007 | Lancaster et al. |
| 2009/0083207 A1 | 3/2009 | Aparicio, IV |
| 2011/0161857 A1* | 6/2011 | Kramer ................. G06T 11/206 715/772 |
| 2011/0295622 A1* | 12/2011 | Farooq ................... G06Q 10/10 705/3 |
| 2011/0313788 A1 | 12/2011 | Amland et al. |
| 2012/0065987 A1* | 3/2012 | Farooq ................. G06F 19/328 705/2 |
| 2015/0039486 A1* | 2/2015 | Huynh ................... G06Q 40/04 705/37 |
| 2016/0313296 A1* | 10/2016 | Bjugstad .......... G01N 33/48707 |
| 2016/0358282 A1 | 12/2016 | Gopal et al. |

(Continued)

OTHER PUBLICATIONS

Engineering Statistics Handbook, sec. 1.3.3.14: Histograms, Oct. 2013, p. 1 (Year: 2013).*

(Continued)

*Primary Examiner* — Eric Nilsson
*Assistant Examiner* — Urmana Islam
(74) *Attorney, Agent, or Firm* — Jordan IP Law, LLC

(57) ABSTRACT

Systems, apparatuses and methods may provide for technology that assigns confidence levels to data bins containing similarity data and length of stay data, wherein the similarity data and the length of stay data correspond to a plurality of previous admissions. Additionally, the confidence levels may be weighted based on a distribution metric that assigns higher weights to denser regions. A length of stay of a target admission may be predicted based on the weighted confidence levels.

24 Claims, 9 Drawing Sheets

(56) References Cited

U.S. PATENT DOCUMENTS

2017/0269104 A1* 9/2017 Montaner Viallonga ................... G01N 33/48

OTHER PUBLICATIONS

Huang, Z. et al., "Length of stay prediction for clinical treatment process using temporal similarity", Expert Systems with Applications, vol. 40, Issue 16, Nov. 15, 2013, pp. 6330-6339.
Alistair E.W. Johnson et al., "Data Descriptor: MIMIC-III, a freely accessible critical care database", Scientific Data, May 24, 2016, 9 pages, 3:160035.
Saffron, "Improving Diagnosis Accuracy and Saving Lives", Saffron Technology, 2014, 2 pages.
International Preliminary Report on Patentability for International Patent Application No. PCT/US2017/061998, dated Jul. 11, 2019, 8 pages.

* cited by examiner

| Patient | Bin_mean | Mean_similarity | Bin_weight | Conf_similarity | Weighted_conf | Bins | Similarity Data |
|---|---|---|---|---|---|---|---|
| A | 7.92 | 0.91 | 0.8 | 0.33 | 0.24 | 5,5,5,5,5,10,10,10,10,10,10 | 0.83,0.83,0.83,0.92,0.92,1.00,0.83,0.83,0.92,0.92,0.92,1.00,1.00 |
| A | 15 | 1 | 0.07 | 0.36 | 0.030 | 15 | 1.00 |
| A | 25 | 0.88 | 0.13 | 0.31 | 0.040 | 25,25 | 0.83,0.92 |
| B | 0 | 0.75 | 0.07 | 0.24 | 0.020 | 0 | 0.75 |
| B | 12 | 0.83 | 0.33 | 0.26 | 0.090 | 10,10,10,15,15 | 0.75,0.75,1.00,0.75,0.92 |
| B | 22.5 | 0.76 | 0.4 | 0.24 | 0.100 | 20,20,20,25,25,25 | 0.75,0.75,0.75,0.75,0.75,0.83 |
| B | 33.3 | 0.81 | 0.2 | 0.26 | 0.050 | 30,35,35 | 0.75,0.75,092 |
| C | 6.79 | 0.87 | 0.93 | 0.46 | 0.40 | 5,5,5,5,5,5,5,10,10,10,10 | 0.86,0.86,0.86,0.86,0.86,0.86,0.86,0.86,1.00,0.86,0.86,0.86,0.86,0.86 |
| C | 15 | 1 | 0.07 | 0.54 | 0.040 | 15 | 1.00 |

| Patient | Predicted_los | Mean_similarity | Bin_weight | Conf_similarity | Weighted_conf | Status |
|---|---|---|---|---|---|---|
| A | 10 | 0.91 | 0.8 | 0.33 | 0.24 | Matched |
| A | 15 | 1 | 0.07 | 0.36 | 0.030 | |
| A | 25 | 0.88 | 0.13 | 0.31 | 0.040 | |
| B | 5 | 0.75 | 0.07 | 0.24 | 0.020 | |
| B | 10 | 0.83 | 0.33 | 0.26 | 0.090 | |
| B | 20 | 0.76 | 0.4 | 0.24 | 0.100 | Matched |
| B | 35 | 0.81 | 0.2 | 0.26 | 0.050 | |
| C | 5 | 0.87 | 0.93 | 0.46 | 0.40 | Matched |
| C | 15 | 1 | 0.07 | 0.54 | 0.040 | |

AUTOMATIC PREDICTION OF PATIENT LENGTH OF STAY AND DETECTION OF MEDICAL CENTER READMISSION DIAGNOSES

TECHNICAL FIELD

Embodiments generally relate to medical center automation technology. More particularly, embodiments relate to technology that automatically predicts patient length of stay and automatically detects medical center readmission diagnoses in real-time.

BACKGROUND

When a new patient is admitted to a medical center (e.g., hospital, emergency care facility), nurses and/or doctors may provide an estimate of the length of stay of the patient in the medical center based on an initial diagnosis and/or test results. The estimate may be revised over time as procedures are undertaken, medicines are administered and the treatment progresses. Numerous revisions to the length of stay estimate may present difficulties to the medical center, the patient, as well as the patient's family. For example, the uncertainty may hinder efforts to effectively manage medical center resources/manpower.

Moreover, the uncertainty may lower patient morale and prevent the family from effectively planning for the discharge of the patient. Other challenges such as frequent readmissions of the patient to the medical center may also lower morale and increase health care payer and/or provider costs.

BRIEF DESCRIPTION OF THE DRAWINGS

The various advantages of the embodiments will become apparent to one skilled in the art by reading the following specification and appended claims, and by referencing the following drawings, in which:

FIG. 3B is an illustration of an example of a prediction table according to an embodiment;

FIG. 4 is an illustration of an example of a prediction result according to an embodiment;

DESCRIPTION OF EMBODIMENTS

Figure 1:
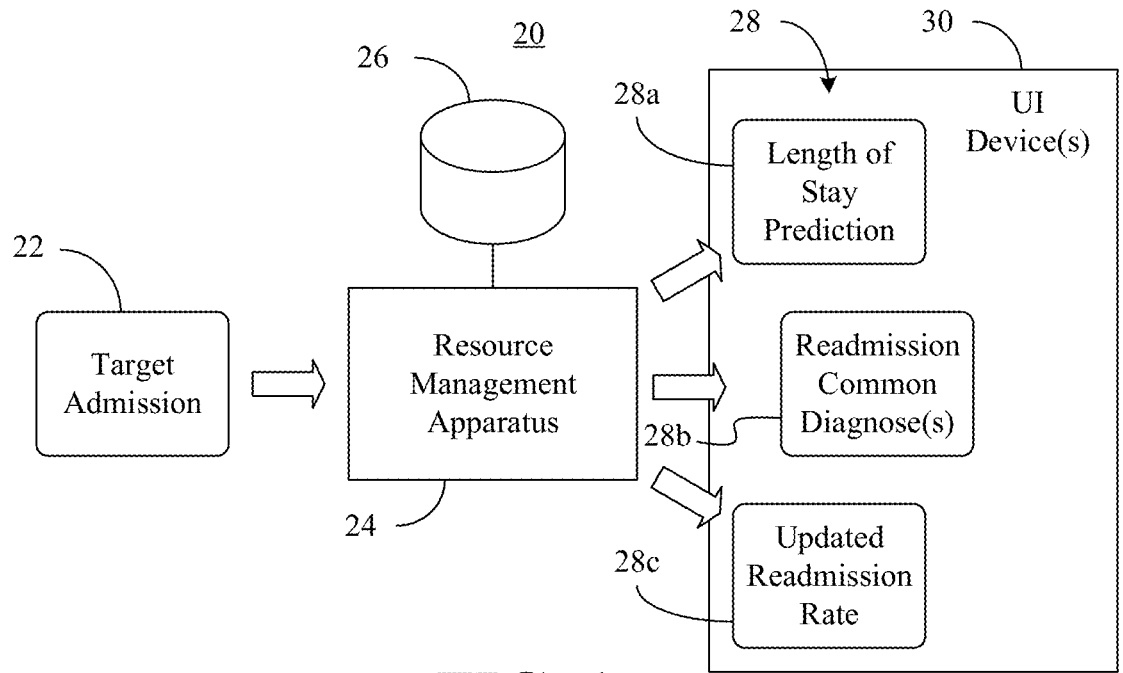
FIG. 1 is a block diagram of an example of a health care computing system according to an embodiment.

Turning now to FIG. 1 a health care computing system 20 that receives information regarding a target admission 22 is shown. The target admission 22 may correspond to a particular "target" patient that is admitted to a hospital, emergency care facility or other medical center. The illustrated system 20 includes a resource management apparatus 24 that queries a data analytics subsystem 26 (e.g., SAFFRON MEMORY BASE/SMB, IBM WATSON, NUMENTA GROK) for information relevant to the target admission 22. The data analytics subsystem 26 may include a currently associated set of data, which may have been brought together by a computer and computer programs to have operations performed on it. Thus, the data analytics subsystem 26 may not necessarily be a managed, constrained set of data (e.g., a data set). Indeed, the data analytics subsystem 26 may in fact be ad hoc for the second, minute, day, etc., and have operations performed on it to produce another data set (e.g., the relevant information). Notwithstanding, the data analytics subsystem 26 may include a traditional database, with distributed data that has an arrangement of a database at any moment in time or it can be grouped in whatever fashion that is conducive to the execution of the methods described herein. As will be discussed in greater detail, the relevant information obtained from the data analytics subsystem 26 might include length of stay data, similarity data, etc., corresponding to other admissions (e.g., admissions of other patients to the medical center).

The illustrated resource management apparatus 24 conducts an automated analysis of the target admission 22 and the information retrieved from the data analytics subsystem 26, and outputs various notifications 28 (28a-28c) via one or more user interface (UI) devices 30 (e.g., display, speaker, printer). The notifications 28 may include, for example, a length of stay prediction 28a that estimates a discharge date for the target patient, one or more readmission common diagnoses 28b that indicate diagnoses in the target admission 22 that are shared with one or more recent admissions of the target patient, an updated readmission rate 28c that indicates the percentage of total admissions to the medical center that are readmissions, and so forth. Accordingly, the notifications 28 may enable more effective management of medical center resources/manpower, provide more certainty to patients and family members, increase patient morale, and reduce health care payer and/or provider costs.

Figure 2:
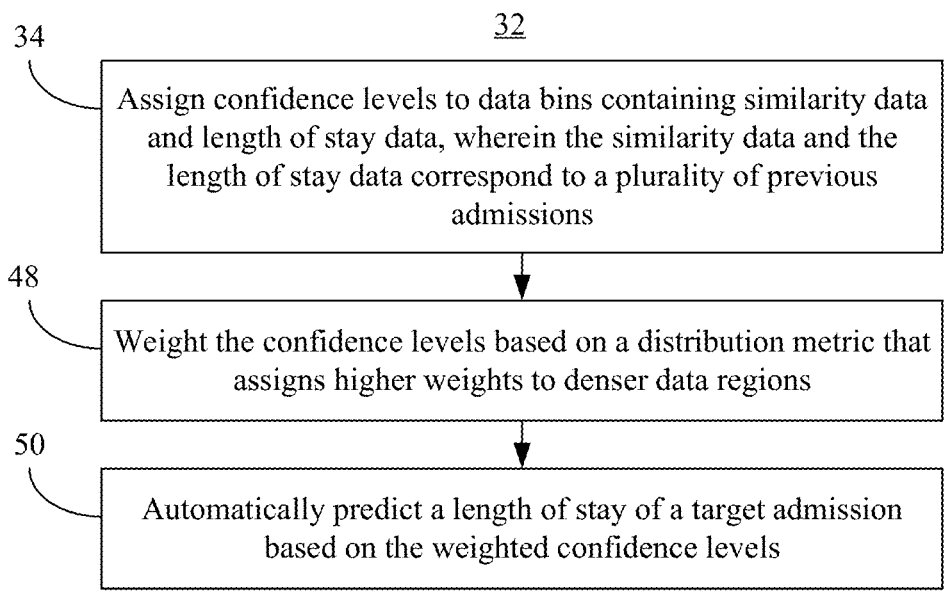
FIG. 2 is a flowchart of an example of a method of operating a resource management apparatus according to an embodiment.

FIG. 2 shows a method 32 of operating a resource management apparatus. The method 32 may generally be implemented in an apparatus such as, for example, the resource management apparatus 24 (FIG. 1), already discussed. More particularly, the method 32 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof.

For example, computer program code to carry out operations shown in method 32 may be written in any combination of one or more programming languages, including an object oriented programming language such as JAVA, SMALLTALK, C++ or the like and conventional procedural programming languages, such as the "C" programming language or similar programming languages. Additionally, logic instructions might include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

In general, previous admissions (e.g., corresponding to other patients) that are similar to a target admission may be identified, along with similarity data and length of stay data corresponding to each previous admission. The length of stay data may indicate how long the other patient was admitted to the medical center and the similarity data may quantify how similar the previous admission is to the target admission (e.g., in terms of diagnosis, urgency, symptoms, etc.). As will be discussed in greater detail, the similarity data and length of stay data may be partitioned into chart data bins according to length of stay. Illustrated processing block 34 assigns confidence levels to the data bins containing the similarity data and the length of stay data. Block 34 may include, for example, determining, for each data bin, an average similarity factor based on the similarity data and determining, for each data bin, a confidence level based on the average similarity factor.

Turning now to 3A, a first stacked bar chart 36 corresponds to a first target patient (e.g., "Patient A"), a second chart 38 corresponds to a second target patient (e.g., "Patient B") and a third chart 40 corresponds to a third target patient (e.g., "Patient C"). In the illustrated example, the first chart 36 is partitioned into a first data bin 42, a second data bin 44 and a third data bin 46. The first data bin 42 may include five previous admissions in which the patients remained in the medical center for five days and seven previous admissions in which the patients remained to the medical center for ten days. The illustrated second data bin 44 includes one previous admission in which the patient remained to the medical center for fifteen days and the illustrated third data bin 46 includes two previous admissions in which the patients remained admitted to the medical center for twenty-five days. The similarity of each previous admission to the target admission is shown in parentheses (i.e., with 1.00 being the maximum).

Figure 3A:
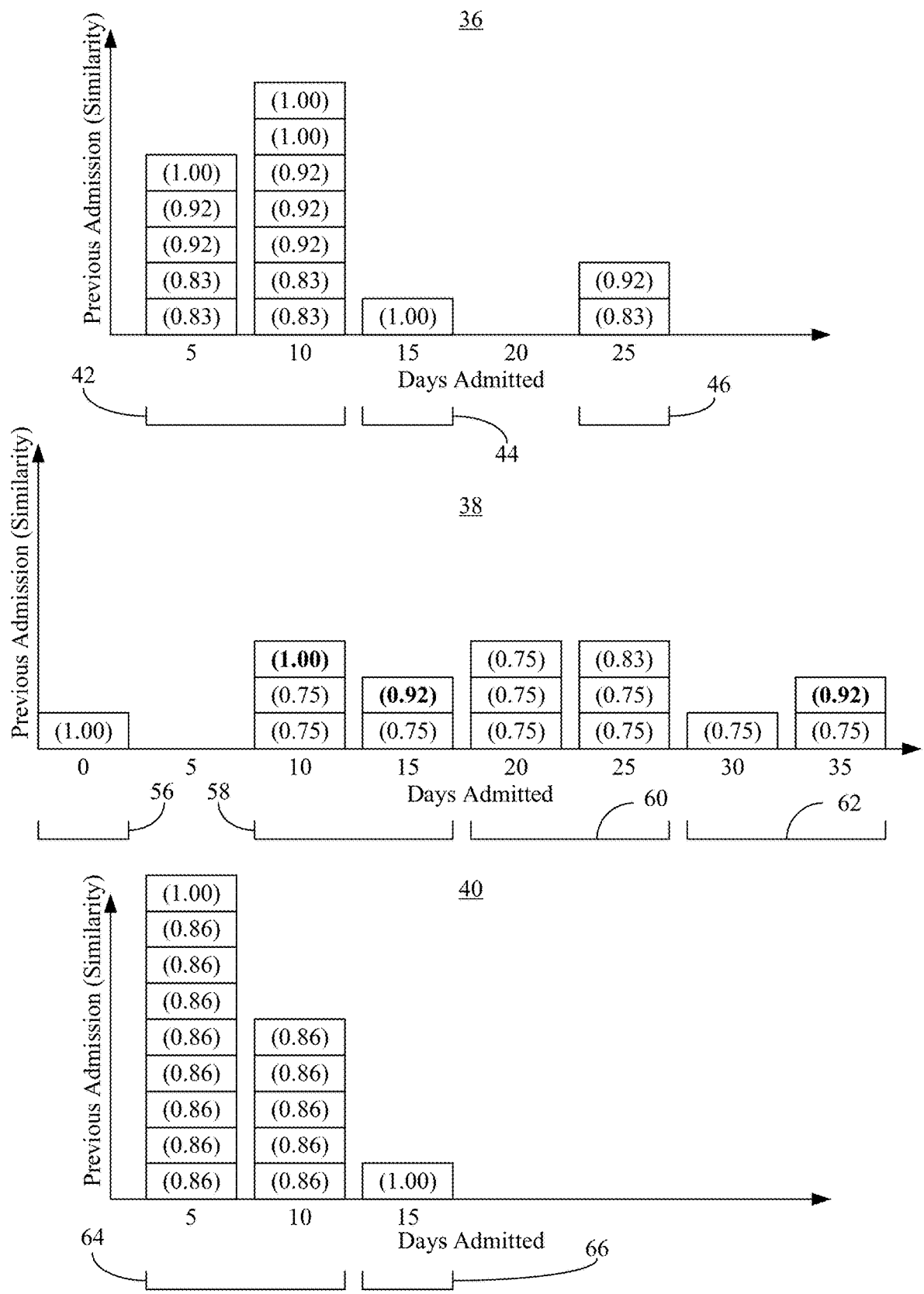
FIG. 3A is a set of plots of examples of chart data bins according to an embodiment.

With continuing reference to FIGS. 2, 3A and 3B, block 34 may determine (e.g., compute) the average similarity factor for the first data bin 42, the average similarity factor for the second data bin 44, the average similarity factor for the third data bin 46, and so forth. As best shown in a prediction table 52 of FIG. 3B, the average similarity factor ("Mean_similarity") is 0.91, 1 and 0.88 for the first, second and third data bins 42, 44, 46, respectively, in the illustrated example. The values provided herein are to facilitate discussion only and may vary depending on the circumstances. Block 34 may also determine (e.g., compute) the confidence level for the first data bin 42, the confidence level for the second data bin 44, the confidence level for the third data bin 46, and so forth. Determining the confidence levels might involve normalizing the data. As best shown in the prediction table 52 of FIG. 3B, the confidence level ("Conf_similarity") is 0.33, 0.36 and 0.31 for the first, second and third data bins 42, 44, 46, respectively, in the illustrated example.

Illustrated processing block 48 provides for weighting the confidence levels based on a distribution metric that assigns higher weights to denser data regions. Block 48 may include determining, for each data bin 42, 44, 46, a fraction of total elements that belong to the data bin 42, 44, 46 and computing a product between the fraction and the confidence level assigned to the data bin 42, 44, 46. As best shown in the prediction table 52 of FIG. 3B, a bin weight ("Bin_weight") of 0.8 may be assigned to the first data bin 42, a bin weight of 0.07 may be assigned to the second data bin 44 and a bin weight of 0.13 may be assigned to the third data bin 46, wherein each bin weight represents the relative density of the bin and the bin weights sum to a value of one. Thus, the illustrated first data bin 42 is assigned the highest bin weight due to the relatively high density of data in the first data bin 42 and the second data bin 44 is assigned the lowest bin weight due to the relatively low density of data in the second data bin 44. Moreover, a weighted confidence ("Weighted_conf") of 0.261 may be computed for the first data bin 42 by multiplying the bin weight (e.g., 0.8) by the confidence level (e.g., 0.33), a weighted confidence of 0.0239 may be computed for the second data bin 44 by multiplying the bin weight (e.g., 0.07) by the confidence level (e.g., 0.36), a weighted confidence of 0.0419 may be computed for the third data bin 46 by multiplying the bin weight (0.13) by the confidence level (e.g., 0.31), and so forth.

Block 50 may automatically predict the length of stay of the target admission based on the weighted confidence levels. Block 50 may include selecting the data bin with the maximum weighted confidence. Thus, in the illustrated example, the first data bin 42 might be selected as the bin providing the optimal length of stay. As best shown in the prediction table 52 of FIG. 3B, a bin average ("Bin_mean") of 7.92 days may be computed for the first data bin 42, a bin average of 15 days may be computed for the second data bin 44, a bin average of 25 days may be computed for the third data bin 46, and so forth. With continuing reference to FIGS. 2, 3A, 3B and 4, a prediction result 54 demonstrates that the first data bin 42 average of 7.92 days may rounded to a prediction value ("Predicted_los") of 10 days, the second data bin 44 may be assigned a prediction value of 15 days and the third data bin 46 may be assigned a prediction value of 25 days. Accordingly, the prediction value of the first data bin 42 (i.e., 10 days) may be flagged with a "Matched" status. Testing the illustrated result in the MIMIC III (Medical Information Mart for Intensive Care III) database reveals that the predicted value is highly accurate.

Similarly, the second histogram chart 38 may be partitioned into a first data bin 56, a second data bin 58, a third data bin 60 and a fourth data bin 62. The first data bin 56 may include one previous admission in which the patient remained in the medical center for zero days. The second data bin 58 may include three previous admissions in which the patients remained in the medical center for ten days and two previous admissions in which the patients remained in the medical center for fifteen days. The illustrated third data bin 60 includes three previous admissions in which the patients remained in the medical center for twenty days and three previous admissions in which the patients remained in the medical center for twenty-five days. Additionally, the fourth data bin 62 might include one previous admission in which the patient remained in the medical center for thirty days and two previous admissions in which the patient remained in the medical center for thirty-five days. Additionally, the third histogram chart 40 may be partitioned into a first data bin 64 and a second data bin 66

With continuing reference to FIGS. 2, 3A, 3B and 4, the prediction result 54 demonstrates that the third data bin 60 may be flagged with a "Matched" status even though other data bins such as the second data bin 58 and the fourth data bin 62 contain similarity values (e.g., in bold) that are higher than the similarity values of the third data bin 60. Testing the illustrated result in the MIMIC III (Medical Information Mart for Intensive Care III) database reveals that the predicted value is highly accurate. Accordingly, the illustrated solution provides unexpectedly accurate results that may substantially enhance the ability of medical centers to manage resources (e.g., improving the operation of the health care computing system).

Figure 5A:
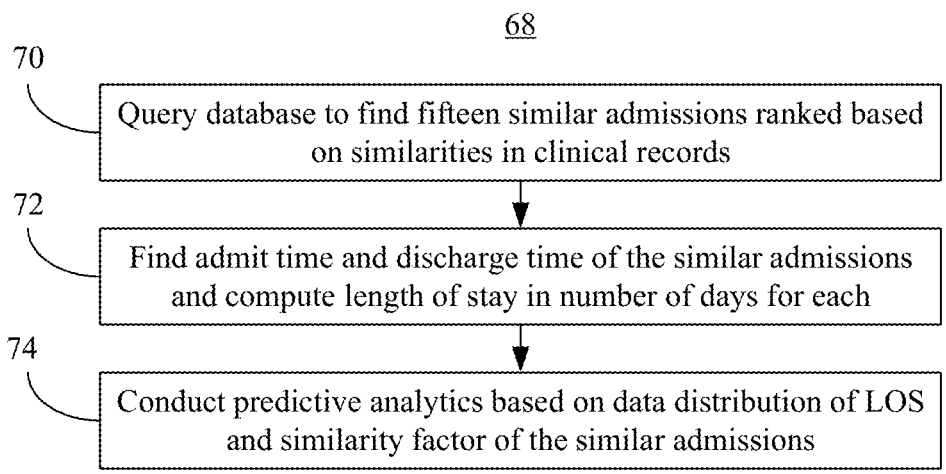
FIG. 5A is a flowchart of an example of a method of using data analytics subsystem queries to generate length of stay predictions according to embodiments.

FIG. 5A shows a more detailed method 68 of using data analytics subsystem queries to generate length of stay predictions. The method 68 may generally be implemented in an apparatus such as, for example, the resource management apparatus 24 (FIG. 1), already discussed. More particularly, the method 68 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated processing block 70 provides for querying a data analytics subsystem to find, for example, fifteen similar admissions ranked (e.g., using the Kolmogorov complexity measure) based on similarities in clinical records. The rankings may use diagnosis, urgency, symptom, and so forth, as inputs. Inputs may also include physiological parameters and unstructured data such as, for example, nurse notes on family history, allergies, etc. Block 72 may find the admit time and the discharge time of the similar admissions and compute the length of stay in number of days for each. Thus, blocks 70 and 72 may both involve searching a data analytics subsystem such as, for example, the SMB via a suitable API (application programming interface). Illustrated block 74 conducts predictive analytics based on the data distribution of the length of stay (LOS) and similarity factor of the similar admissions. The output of block 74 may be a predicted hospital stay duration and/or discharge date of a target patient at the target admission.

Figure 5B:
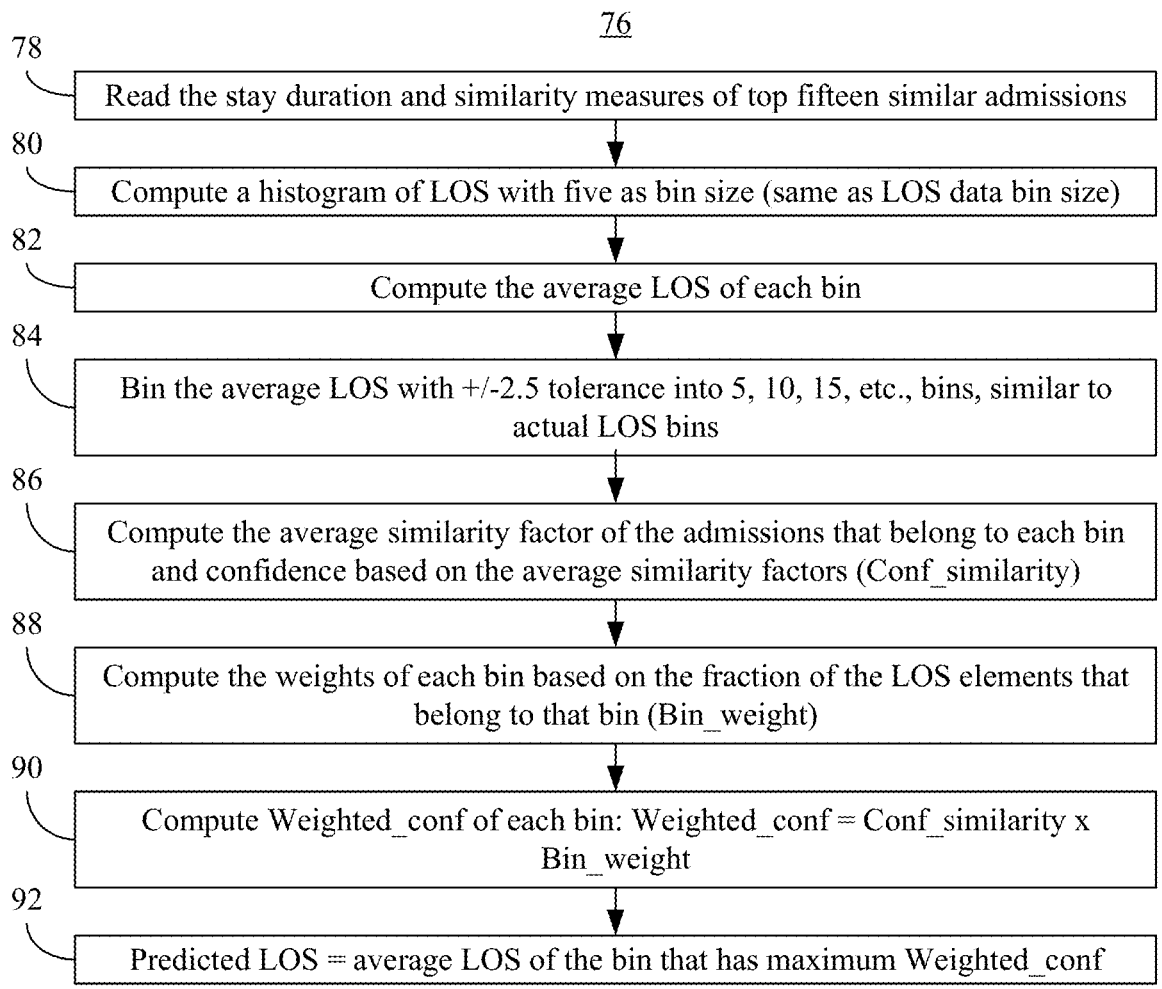
FIG. 5B is a flowchart of an example of a method of using data bins to conduct predictive analytics according to an embodiment.

FIG. 5B shows a more detailed method 76 of using data bins to conduct predictive analytics. The method 76 may generally be substituted for block 74 (FIG. 5A), already discussed. More particularly, the method 76 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated processing block 78 provides for reading the stay duration and similarity measures for the top fifteen similar admissions, wherein a histogram of LOS may be computed at block 80 with five days as a bin width/size (e.g., the same as the LOS data bin size). Additionally, the average LOS of each bin may be computed at block 82. Block 84 may bin the average LOS with +/−2.5 tolerance into five, ten, fifteen, etc., bins (e.g., similar to the actual LOS bins).

Illustrated block 86 computes the average similarity factor of the admissions that belong to each bin and confidence (e.g., Conf_similarity) based on the average similarity factors. In addition, the weights of each bin (e.g., Bin_weight) may be computed at block 88 based on the fraction of the LOS elements that belong to that bin. Block 90 may compute Weighted_conf of each bin as: Weighted_conf=Conf_similarity×Bin_weight. Moreover, illustrated block 92 selects the predicted LOS as the average LOS of the bin that has the maximum Weighted_conf.

Figure 6:
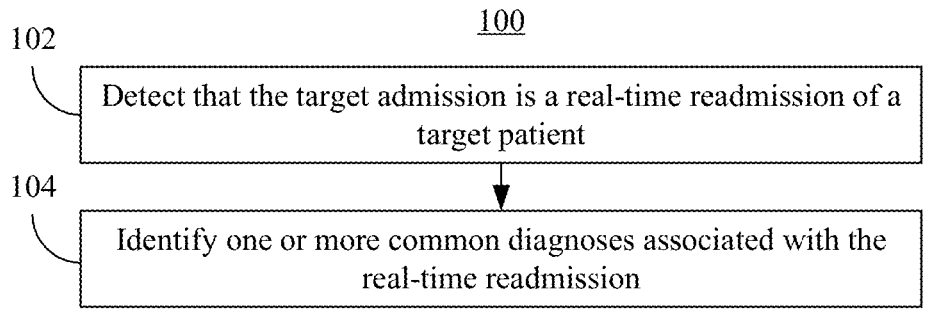
FIG. 6 is a flowchart of an example of a method of automatically detecting readmissions according to an embodiment.

FIG. 6 shows a method 100 of automatically detecting readmissions. The method 100 may generally be implemented in an apparatus such as, for example, the resource management apparatus 24 (FIG. 1), already discussed. More particularly, the method 100 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated processing block 102 detects that the target admission is a real-time readmission of a target patient. Block 102 may include computing a difference between an admission time of the target admission and admission time of a previous admission associated with the target patient and detecting that the difference does not exceed a threshold (e.g., thirty days). Illustrated block 104 identifies one or more common diagnoses associated with the real-time readmission.

Figure 7:
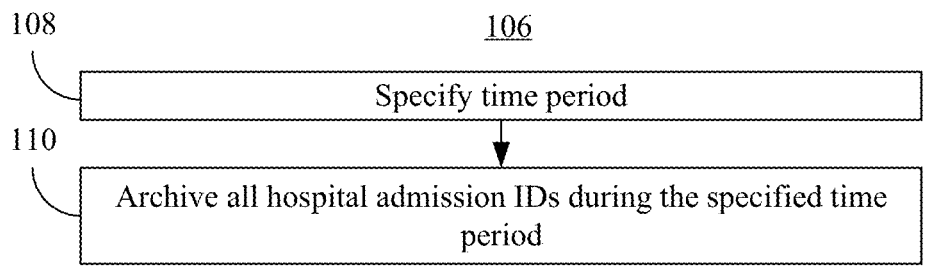
FIG. 7 is a flowchart of an example of a method of collecting patient record information according to an embodiment.

FIG. 7 shows a method 106 of collecting patient record information. The method 106 may generally be implemented in an apparatus such as, for example, the resource management apparatus 24 (FIG. 1), already discussed. More particularly, the method 106 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof. Illustrated block 108 provides for specifying a time period, wherein all hospital admission identifiers (IDs) may be archived during the specified time period at block 110.

Figure 8:
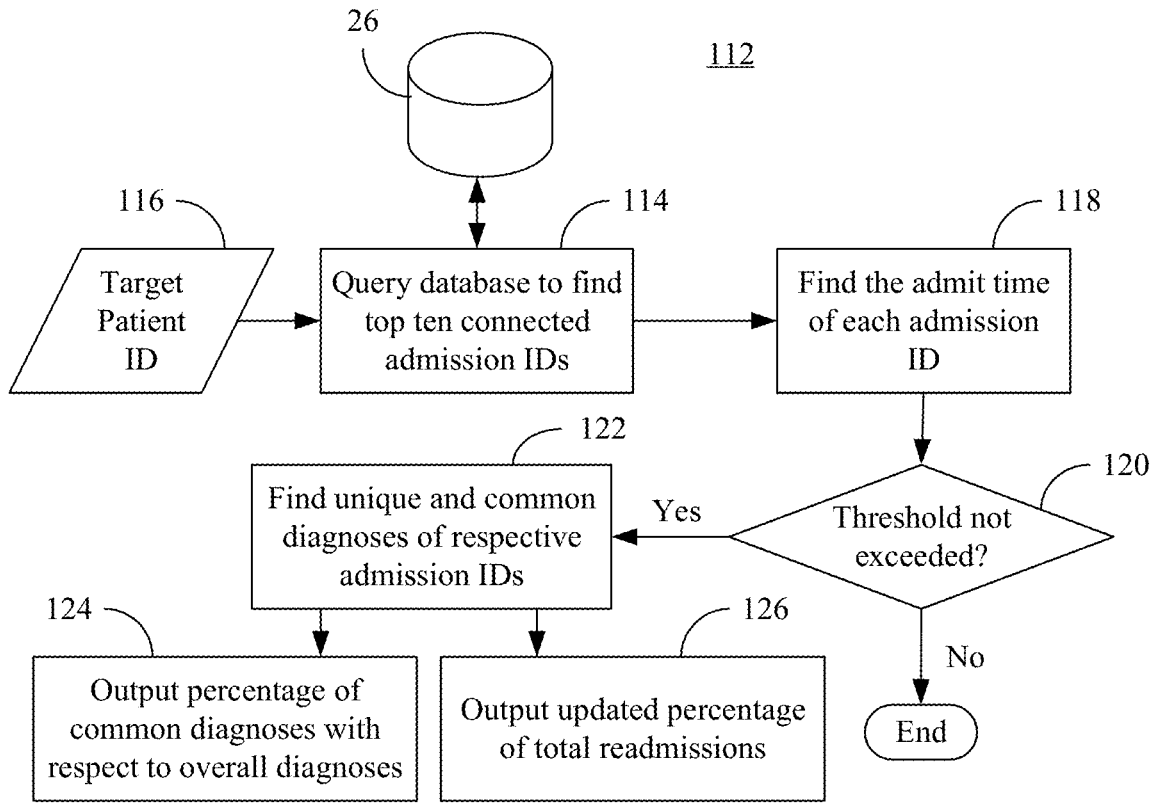
FIG. 8 is a flowchart of an example of a method of generating readmission notifications according to an embodiment.

FIG. 8 shows a method 112 of generating readmission notifications. The method 112 may generally be implemented in an apparatus such as, for example, the resource management apparatus 24 (FIG. 1), already discussed. More particularly, the method 112 may be implemented in one or more modules as a set of logic instructions stored in a machine- or computer-readable storage medium such as RAM, ROM, PROM, firmware, flash memory, etc., in configurable logic such as, for example, PLAs, FPGAs, CPLDs, in fixed-functionality logic hardware using circuit technology such as, for example, ASIC, CMOS or TTL technology, or any combination thereof.

Illustrated block 114 may receive a target patient ID 116 and query the data analytics subsystem 26 to find the top ten connected admission IDs. Each of the connected admission IDs may therefore correspond to a previous admission of the particular target patient to the medical center. Block 118 may find the admit time of each admission ID, wherein illustrated block 120 computes the difference between the admit time of the previous admission and the admit time of the target admission. If it is determined at block 120 that a threshold (e.g., thirty days) is exceeded, a real-time readmission has not been detected and the illustrated method 112 terminates. If it is determined at block 120 that the threshold is not exceeded, a real-time readmission has been detected and illustrated block 122 finds unique and common diagnoses of the readmission (e.g., the respective admission IDs). Block 124 may use the unique and common diagnoses to determine and output the percentage of common diagnoses with respect to overall diagnoses (e.g., the ration between the common diagnoses and total diagnoses associated with the real-time readmission). Table I below illustrates an example of such an output.

TABLE I

| Admission ID1 | Admission ID2 | Admission Date1 | Admission Date2 | Diff | Common | Unique | % Common |
|---|---|---|---|---|---|---|---|
| 159999 | 180026 | 1/15/2143 | 1/5/2143 | 10 | Condition A, Condition, C, Condition E, Condition F, Condition G | Condition A, Condition B, Condition C, Condition, D, Condition E, Condition F, Condition G | 71.43% |
| 171835 | 104433 | 2/23/2179 | 3/9/2179 | 14 | Condition H, Condition J, Condition K, Condition, L | Condition H, Condition I, Condition J, Condition K, Condition L | 80.00% |

Figure 9:
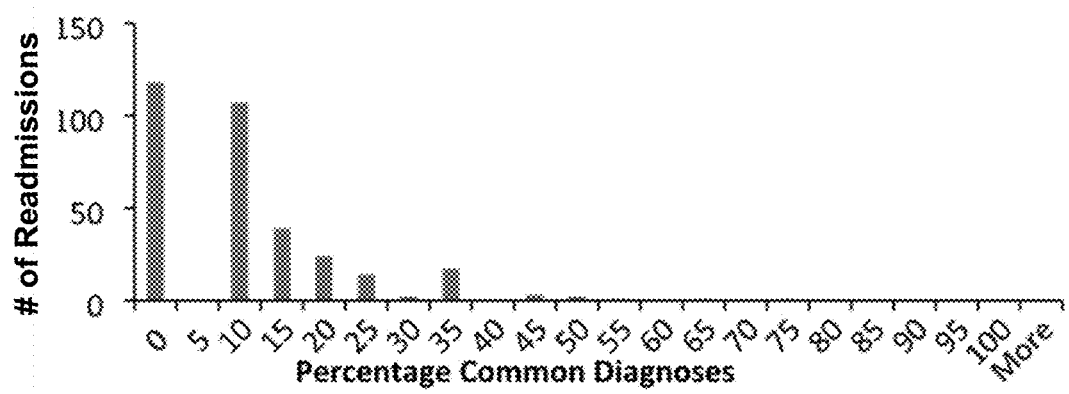
FIG. 9 is an illustration of an example of a common diagnosis analysis result according to an embodiment.

Illustrated block 126 outputs an updated percentage of total readmissions. FIG. 9 shows an example output 128 of block 126 (FIG. 8) in which the number of readmission cases is displayed along with their percentage of common diagnoses. The output 128 might be monitored for spikes in common diagnoses in order detect diagnosis-specific issues as early as possible.

Figure 10:
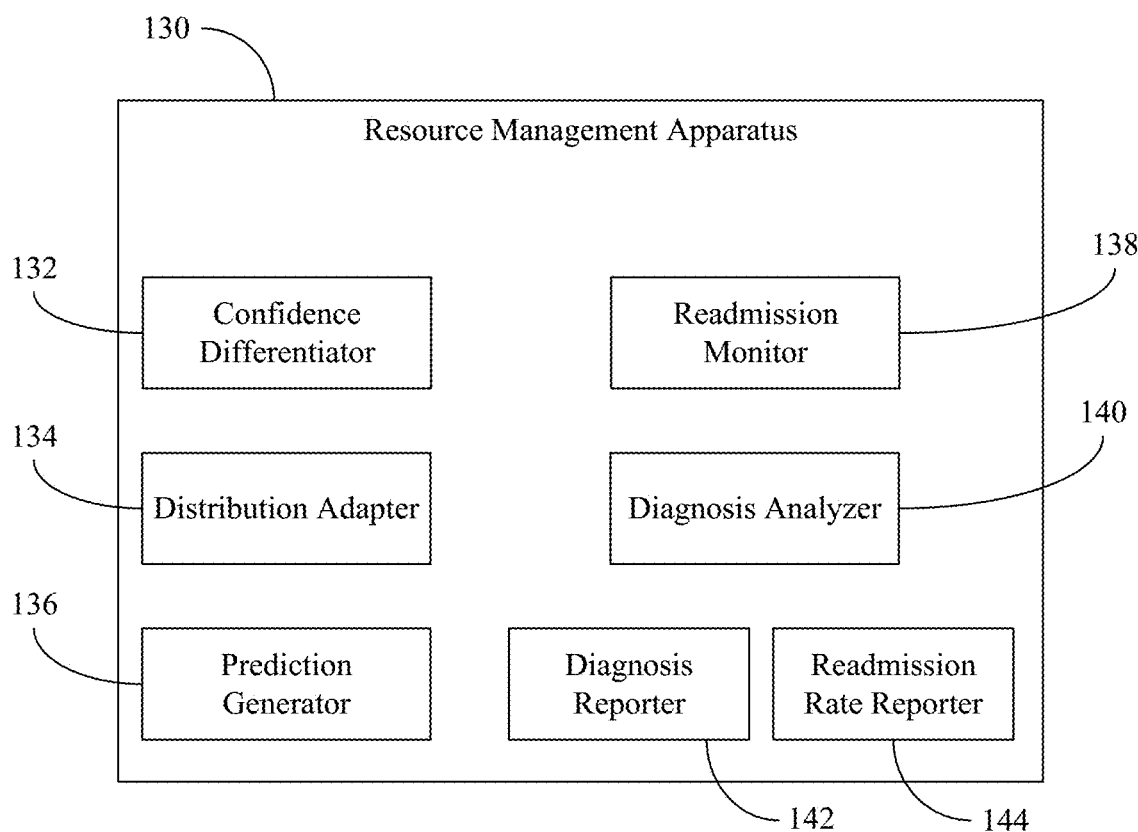
FIG. 10 is a block diagram of an example of a resource management apparatus according to an embodiment.

FIG. 10 shows a resource management apparatus 130 that may be readily substituted for the apparatus 24 (FIG. 1), already discussed. The apparatus 130, may include logic instructions, configurable logic, fixed-functionality logic hardware, etc., or any combination thereof, wherein the components of the apparatus 130 may be communicatively coupled to one another via buses, switching fabrics, control registers, etc., or any combination thereof. The illustrated apparatus 130 includes a confidence differentiator 132 to assign confidence levels to data bins containing similarity data and length of stay data, wherein the similarity data and the length of stay data is to correspond to a plurality of previous admissions. The confidence differentiator 132 may determine for each data bin, an average similarity factor based on the similarity data, and determine, for each data bin, a confidence level based on the average similarity factor.

Additionally, a distribution adapter 134 that is communicatively coupled to the confidence differentiator 132 may weight the confidence levels based on a distribution metric that assigns higher weights to denser data regions. In one example, the distribution adapter 134 determines, for each data bin, a fraction of total elements that belong to the data bin, and computes a product between the fraction and the confidence level assigned to the data bin. The illustrated apparatus 130 also includes a prediction generator 136 communicatively coupled to the distribution adapter 134. The prediction generator 136 may automatically predict a length of stay of a target admission based on the weighted confidence levels. The output of the prediction generator 136 may be conveyed to one or more users via a user interface device such as, for example, the UI device(s) 30 (FIG. 1), already discussed.

The apparatus 130 may further include a readmission monitor 138 to detect that the target admission is a real-time readmission of a particular target patient. In one example, the readmission monitor 138 computes the difference between an admission time of the target admission and an admission time of a previous admission associated with the target patient. The readmission monitor 138 may also detect that the difference does not exceed a threshold. The illustrated apparatus 130 also includes a diagnosis analyzer 140 communicatively coupled to the readmission monitor 138, wherein the diagnosis analyzer 140 is to identify one or more common diagnoses associated with the real-time readmission. The apparatus 130 may also include a diagnosis reporter 142 to determine a ratio between the common diagnoses and total diagnoses associated with the real-time admission. Moreover, a readmission rate reporter 144 may update a percentage of total readmissions based on the common diagnoses. The output of the diagnosis reporter 142 and/or the readmission rate reporter 144 may be conveyed to one or more users via a user interface device such as, for example, the UI device(s) 30 (FIG. 1), already discussed.

Figure 11:
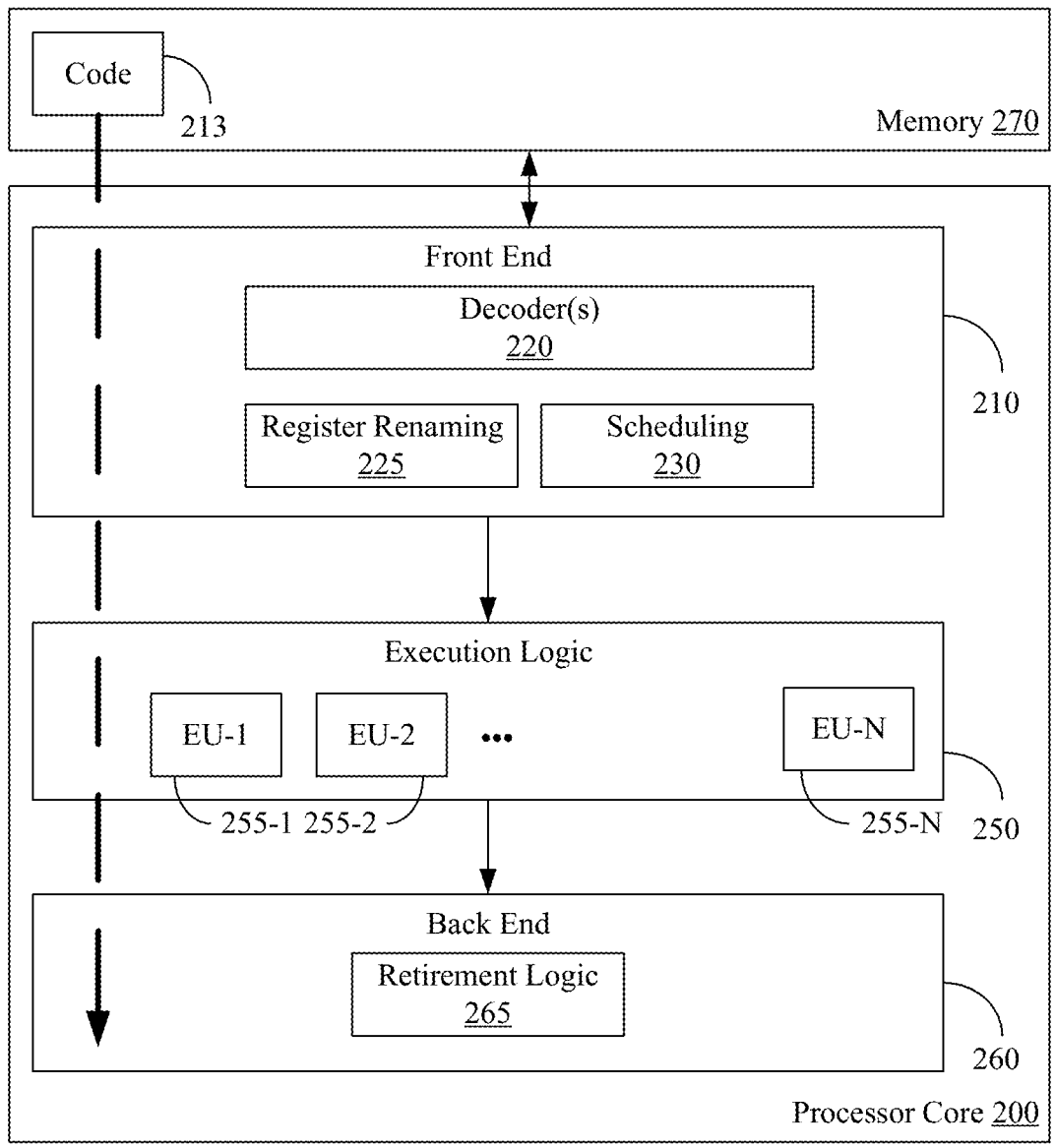
FIG. 11 is a block diagram of an example of a processor according to an embodiment.

FIG. 11 illustrates a processor core 200 according to one embodiment. The processor core 200 may be the core for any type of processor, such as a micro-processor, an embedded processor, a digital signal processor (DSP), a network processor, or other device to execute code. Although only one processor core 200 is illustrated in FIG. 11, a processing element may alternatively include more than one of the processor core 200 illustrated in FIG. 11. The processor core 200 may be a single-threaded core or, for at least one embodiment, the processor core 200 may be multithreaded in that it may include more than one hardware thread context (or "logical processor") per core.

FIG. 11 also illustrates a memory 270 coupled to the processor core 200. The memory 270 may be any of a wide variety of memories (including various layers of memory hierarchy) as are known or otherwise available to those of skill in the art. The memory 270 may include one or more code 213 instruction(s) to be executed by the processor core 200, wherein the code 213 may implement the method 32 (FIG. 2), the method 68 (FIG. 5A), the method 76 (FIG. 5B), the method 100 (FIG. 6), the method 106 (FIG. 70), and/or the method 112 (FIG. 8), already discussed. The processor core 200 follows a program sequence of instructions indicated by the code 213. Each instruction may enter a front end portion 210 and be processed by one or more decoders 220. The decoder 220 may generate as its output a micro operation such as a fixed width micro operation in a predefined format, or may generate other instructions, microinstructions, or control signals which reflect the original code instruction. The illustrated front end portion 210 also includes register renaming logic 225 and scheduling logic 230, which generally allocate resources and queue the operation corresponding to the convert instruction for execution.

The processor core 200 is shown including execution logic 250 having a set of execution units 255-1 through 255-N. Some embodiments may include a number of execution units dedicated to specific functions or sets of functions. Other embodiments may include only one execution unit or one execution unit that can perform a particular function. The illustrated execution logic 250 performs the operations specified by code instructions.

After completion of execution of the operations specified by the code instructions, back end logic 260 retires the instructions of the code 213. In one embodiment, the processor core 200 allows out of order execution but requires in order retirement of instructions. Retirement logic 265 may take a variety of forms as known to those of skill in the art (e.g., re-order buffers or the like). In this manner, the processor core 200 is transformed during execution of the code 213, at least in terms of the output generated by the decoder, the hardware registers and tables utilized by the register renaming logic 225, and any registers (not shown) modified by the execution logic 250.

Although not illustrated in FIG. 11, a processing element may include other elements on chip with the processor core 200. For example, a processing element may include memory control logic along with the processor core 200. The processing element may include I/O control logic and/or may include I/O control logic integrated with memory control logic. The processing element may also include one or more caches.

Figure 12:
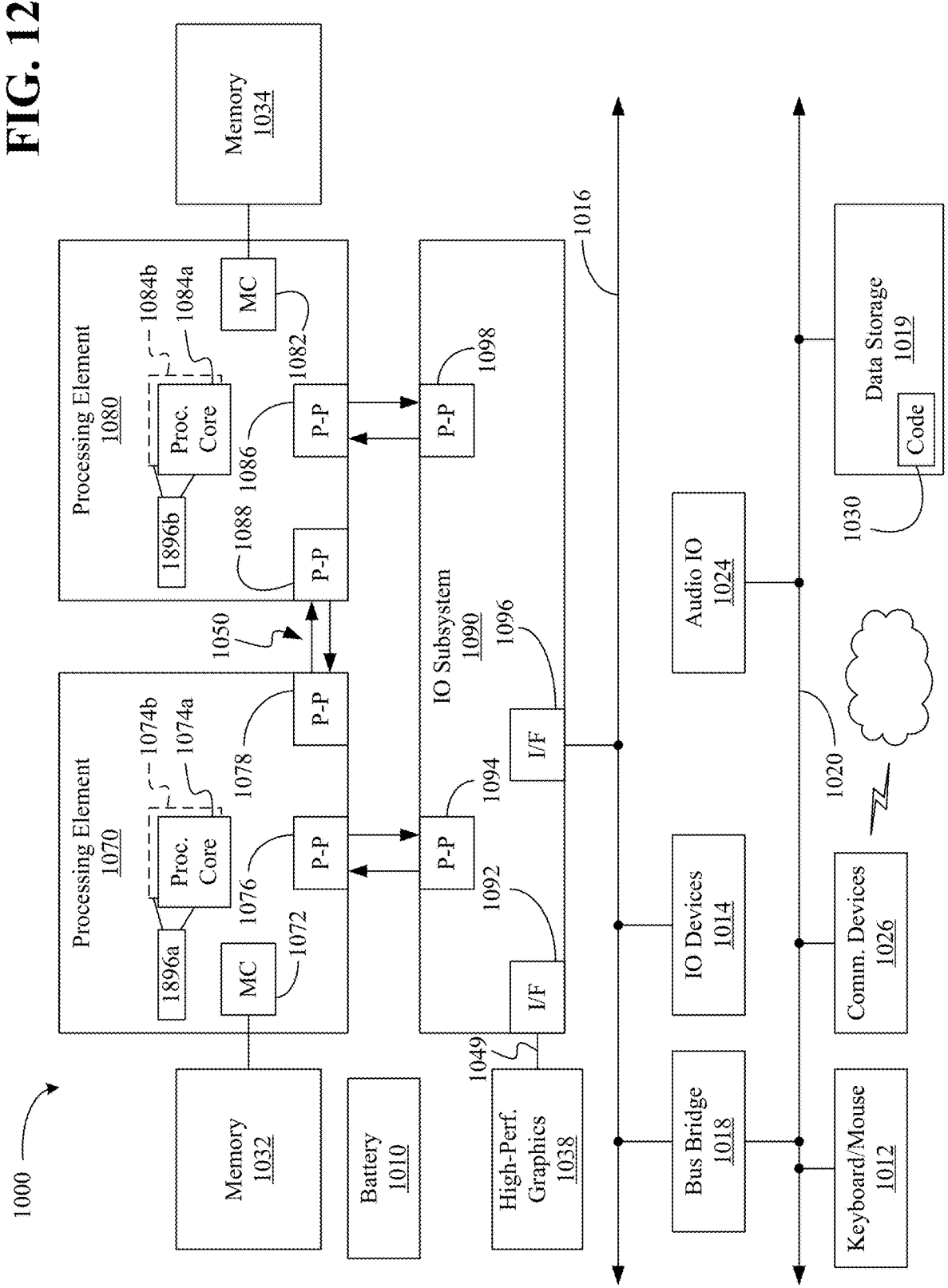
FIG. 12 is a block diagram of an example of a computing system according to an embodiment.

Referring now to FIG. 12, shown is a block diagram of a computing system 1000 embodiment in accordance with an embodiment. Shown in FIG. 12 is a multiprocessor system 1000 that includes a first processing element 1070 and a second processing element 1080. While two processing elements 1070 and 1080 are shown, it is to be understood that an embodiment of the system 1000 may also include only one such processing element.

The system 1000 is illustrated as a point-to-point interconnect system, wherein the first processing element 1070 and the second processing element 1080 are coupled via a point-to-point interconnect 1050. It should be understood that any or all of the interconnects illustrated in FIG. 12 may be implemented as a multi-drop bus rather than point-to-point interconnect.

As shown in FIG. 12, each of processing elements 1070 and 1080 may be multicore processors, including first and second processor cores (i.e., processor cores 1074a and 1074b and processor cores 1084a and 1084b). Such cores 1074a, 1074b, 1084a, 1084b may be configured to execute instruction code in a manner similar to that discussed above in connection with FIG. 11.

Each processing element 1070, 1080 may include at least one shared cache 1896a, 1896b. The shared cache 1896a, 1896b may store data (e.g., instructions) that are utilized by one or more components of the processor, such as the cores 1074a, 1074b and 1084a, 1084b, respectively. For example, the shared cache 1896a, 1896b may locally cache data stored in a memory 1032, 1034 for faster access by components of the processor. In one or more embodiments, the shared cache 1896a, 1896b may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the embodiments are not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to processor a first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, micro architectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

The first processing element 1070 may further include memory controller logic (MC) 1072 and point-to-point (P-P) interfaces 1076 and 1078. Similarly, the second processing element 1080 may include a MC 1082 and P-P interfaces 1086 and 1088. As shown in FIG. 12, MC's 1072 and 1082 couple the processors to respective memories, namely a memory 1032 and a memory 1034, which may be portions of main memory locally attached to the respective processors. While the MC 1072 and 1082 is illustrated as integrated into the processing elements 1070, 1080, for alternative embodiments the MC logic may be discrete logic outside the processing elements 1070, 1080 rather than integrated therein.

The first processing element 1070 and the second processing element 1080 may be coupled to an I/O subsystem 1090 via P-P interconnects 1076 1086, respectively. As shown in FIG. 12, the I/O subsystem 1090 includes P-P interfaces 1094 and 1098. Furthermore, I/O subsystem 1090 includes an interface 1092 to couple I/O subsystem 1090 with a high performance graphics engine 1038. In one embodiment, bus 1049 may be used to couple the graphics engine 1038 to the I/O subsystem 1090. Alternately, a point-to-point interconnect may couple these components.

In turn, I/O subsystem 1090 may be coupled to a first bus 1016 via an interface 1096. In one embodiment, the first bus 1016 may be a Peripheral Component Interconnect (PCI) bus, or a bus such as a PCI Express bus or another third generation I/O interconnect bus, although the scope of the embodiments are not so limited.

As shown in FIG. 12, various I/O devices 1014 (e.g., biometric scanners, speakers, cameras, sensors) may be coupled to the first bus 1016, along with a bus bridge 1018 which may couple the first bus 1016 to a second bus 1020. In one embodiment, the second bus 1020 may be a low pin count (LPC) bus. Various devices may be coupled to the second bus 1020 including, for example, a keyboard/mouse 1012, communication device(s) 1026, and a data storage unit 1019 such as a disk drive or other mass storage device which may include code 1030, in one embodiment. The illustrated code 1030 may implement the method 32 (FIG. 2), the method 68 (FIG. 5A), the method 76 (FIG. 5B), the method 100 (FIG. 6), the method 106 (FIG. 7O), and/or the method 112 (FIG. 8), already discussed. Further, an audio I/O 1024 may be coupled to second bus 1020 and a battery 1010 may supply power to the computing system 1000.

Note that other embodiments are contemplated. For example, instead of the point-to-point architecture of FIG. 12, a system may implement a multi-drop bus or another such communication topology. Also, the elements of FIG. 12 may alternatively be partitioned using more or fewer integrated chips than shown in FIG. 12.

Additional Notes and Examples

Example 1 may include a health care computing system comprising a data analytics subsystem to generate, in response to a query, similarity data and length of stay data corresponding to a plurality of previous admissions, a resource management apparatus including a confidence differentiator to assign confidence levels to data bins containing the similarity data and the length of stay data, a distribution adapter communicatively coupled to the confidence differentiator, the distribution adapter to weight the confidence levels based on a distribution metric that assigns higher weights to denser data regions, and a prediction generator communicatively coupled to the distribution adapter, the prediction generator to automatically predict a length of stay of a target admission based on the weighted confidence levels, and a user interface device communicatively coupled to the resource management apparatus, the user interface device to output the predicted length of stay.

Example 2 may include the system of Example 1, wherein the distribution adapter is to determine, for each data bin, a fraction of total elements that belong to the data bin, and compute a product between the fraction and a confidence level assigned to the data bin.

Example 3 may include the system of Example 1, wherein the confidence differentiator is to determine, for each data bin, an average similarity factor based on the similarity data, and determine, for each data bin, a confidence level based on the average similarity factor.

Example 4 may include the system of any one of Examples 1 to 3, wherein the resource management apparatus further includes a readmission monitor to detect that the target admission is a real-time readmission of a target patient, and a diagnosis analyzer communicatively coupled to the readmission monitor, the diagnosis analyzer to identify one or more common diagnoses associated with the real-time readmission.

Example 5 may include the system of any Example 4, wherein the readmission monitor is to compute a difference between an admission time of the target admission and an admission time of a previous admission associated with the target patient, and detect that the difference does not exceed a threshold.

Example 6 may include the system of Example 4, wherein the resource management apparatus further includes a diagnosis reporter to determine a ratio between the one or more common diagnoses and total diagnoses associated with the real-time admission, and a readmission rate reporter to update a percentage of total readmissions based on the one or more common diagnoses.

Example 7 may include a resource management apparatus comprising a confidence differentiator to assign confidence levels to data bins containing similarity data and length of stay data, wherein the similarity data and the length of stay data is to correspond to a plurality of previous admissions, a distribution adapter communicatively coupled to the confidence differentiator, the distribution adapter to weight the confidence levels based on a distribution metric that assigns higher weights to denser data regions, and a prediction generator communicatively coupled to the distribution adapter, the prediction generator to automatically predict a length of stay of a target admission based on the weighted confidence levels.

Example 8 may include the apparatus of Example 7, wherein the distribution adapter is to determine, for each data bin, a fraction of total elements that belong to the data bin, and compute a product between the fraction and a confidence level assigned to the data bin.

Example 9 may include the apparatus of Example 7, wherein the confidence differentiator is to determine, for each data bin, an average similarity factor based on the similarity data, and determine, for each data bin, a confidence level based on the average similarity factor.

Example 10 may include the apparatus of any one of Examples 7 to 9, further including a readmission monitor to detect that the target admission is a real-time readmission of a target patient, and a diagnosis analyzer communicatively coupled to the readmission monitor, the diagnosis analyzer to identify one or more common diagnoses associated with the real-time readmission.

Example 11 may include the apparatus of Example 10, wherein the readmission monitor is to compute a difference between an admission time of the target admission and an admission time of a previous admission associated with the target patient, and detect that the difference does not exceed a threshold.

Example 12 may include the apparatus of Example 10, further including a diagnosis reporter to determine a ratio between the one or more common diagnoses and total diagnoses associated with the real-time admission, and a readmission rate reporter to update a percentage of total readmissions based on the one or more common diagnoses.

Example 13 may include a method of operating a resource management apparatus, comprising assigning confidence levels to data bins containing similarity data and length of stay data, wherein the similarity data and the length of stay data correspond to a plurality of previous admissions, weighting the confidence levels based on a distribution metric that assigns higher weights to denser data regions, and automatically predicting a length of stay of a target admission based on the weighted confidence levels.

Example 14 may include the method of Example 13, wherein weighting the confidence levels includes determining, for each data bin, a fraction of total elements that belong to the data bin, and computing a product between the fraction and a confidence level assigned to the data bin.

Example 15 may include the method of Example 13, wherein assigning the confidence levels includes determining, for each data bin, an average similarity factor based on the similarity data, and determining, for each data bin, a confidence level based on the average similarity factor.

Example 16 may include the method of any one of Examples 13 to 15, further including detecting that the target admission is a real-time readmission of a target patient, and identifying one or more common diagnoses associated with the real-time readmission.

Example 17 may include the method of Example 16, wherein detecting that the target admission is a real-time readmission includes computing a difference between an admission time of the target admission and an admission time of a previous admission associated with the target patient, and detecting that the difference does not exceed a threshold.

Example 18 may include the method of Example 16, further including determining a ratio between the one or more common diagnoses and total diagnoses associated with the real-time readmission, and updating a percentage of total readmissions based on the one or more common diagnoses.

Example 19 may include at least one computer readable storage medium comprising a set of instructions, which when executed by a computing system, cause the computing system to assign confidence levels to data bins containing similarity data and length of stay data, wherein the similarity data and the length of stay data is to correspond to a plurality of previous admissions, weight the confidence levels based on a distribution metric that assigns higher weights to denser data regions, and automatically predict a length of stay of a target admission based on the weighted confidence levels.

Example 20 may include the at least one computer readable storage medium of Example 19, wherein the instructions, when executed, cause the computing system to determine, for each data bin, a fraction of total elements that belong to the data bin, and compute a product between the fraction and a confidence level assigned to the data bin to weight the confidence levels.

Example 21 may include the at least one computer readable storage medium of Example 19, wherein the instructions, when executed, cause the computing system to determine, for each data bin, an average similarity factor based on the similarity data, and determine, for each data bin, a confidence level based on the average similarity factor to assign the confidence levels.

Example 22 may include the at least one computer readable storage medium of any one of Examples 19 to 21, wherein the instructions, when executed, cause the computing system to detect that the target admission is a real-time readmission of a target patient, and identify one or more common diagnoses associated with the real-time readmission.

Example 23 may include the at least one computer readable storage medium of Example 22, wherein the instructions, when executed, cause the computing system to compute a difference between an admission time of the target admission and an admission time of a previous admission associated with the target patient, and detect that the difference does not exceed a threshold to detect that the target admission is a real-time readmission.

Example 24 may include the at least one computer readable storage medium of Example 22, wherein the instructions, when executed, cause the computing system to determine a ratio between the one or more common diagnoses and total diagnoses associated with the real-time readmission, and update a percentage of total readmissions based on the one or more common diagnoses.

Example 25 may include a resource management apparatus comprising means for assigning confidence levels to data bins containing similarity data and length of stay data, wherein the similarity data and the length of stay data are to correspond to a plurality of previous admissions, means for weighting the confidence levels based on a distribution metric that assigns higher weights to denser data regions, and means for automatically predicting a length of stay of a target admission based on the weighted confidence levels.

Example 26 may include the apparatus of Example 25, wherein the means for weighting the confidence levels includes means for determining, for each data bin, a fraction of total elements that belong to the data bin, and means for computing a product between the fraction and a confidence level assigned to the data bin.

Example 27 may include the apparatus of Example 25, wherein the means for assigning the confidence levels includes means for determining, for each data bin, an average similarity factor based on the similarity data, and means for determining, for each data bin, a confidence level based on the average similarity factor.

Example 28 may include the apparatus of any one of Examples 25 to 27, further including means for detecting that the target admission is a real-time readmission of a target patient, and means for identifying one or more common diagnoses associated with the real-time readmission.

Example 29 may include the apparatus of Example 28, wherein the means for detecting that the target admission is a real-time readmission includes means for computing a difference between an admission time of the target admission and an admission time of a previous admission associated with the target patient, and means for detecting that the difference does not exceed a threshold.

Example 30 may include the apparatus of Example 28, further including means for determining a ratio between the one or more common diagnoses and total diagnoses associated with the real-time readmission, and means for updating a percentage of total readmissions based on the one or more common diagnoses.

Thus, technology described herein may provide a predictive framework that uses cognitive technologies and methods to measure similarities in clinical records (e.g., diagnoses of the new or target patient, his/her admission type such as emergency, elective, urgent etc.) and other attributes (e.g., prescribed drugs, suggested procedures etc.) to identify similar hospital admissions recorded in a clinical data analytics subsystem. The cognitive framework, which may be based on SMB technologies, may compute the similarity factor between the new patient's clinical records and each of the similar hospital admissions present in the data analytics subsystem. The technology may estimate the hospital length of stay of the new patient, based on the data distribution of the hospital stay, durations of the top fifteen most similar hospital admissions and their similarity factors. The generated information may enable more effective scheduling, hospital resource requirement estimations and manpower allocation.

More particularly, the technology is not subjective or prone to personal errors and the estimates are based on the data distribution of a large number of similar patients (e.g., Big Data) identified based on cognitive technologies and methods. Thus, the technology may provide an objective estimate. Moreover, the technology is based on the analysis of data distribution of hospital length of stays of similar patients, along with respective similarity factors, increasing the accuracy of the estimate. Indeed, unexpected prediction accuracies of 87% were achieved. The estimate may exploit the rich clinical records data analytics subsystems of medical centers and hence may improve over time, as more records are added.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the computing system within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A; B; C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
a data analytics subsystem to generate, in response to a query, similarity data and length of stay data that both correspond to a plurality of previous admissions;
a resource management apparatus including:
a confidence differentiator to assign confidence levels to a plurality of data bins containing the similarity data and the length of stay data that both correspond to a plurality of previous admissions of other patients, wherein a first confidence level is assigned to a first data bin that contains similarity data associated within a first length of stay range, and wherein a second confidence level is assigned to a second data bin that contains similarity data within a second length of stay, wherein the second confidence level is different from the first confidence level, and wherein the second length of stay range is different from the first length of stay range,
a distribution adapter communicatively coupled to the confidence differentiator, the distribution adapter to weigh the confidence levels based on a distribution metric that assigns a first weight to a first data region having a first density and assigns a second higher weight to a second data region having a second higher density, wherein each bin weight represents the relative density of one of the plurality of data bins and the bin weights sum to a value of one, and wherein the weighted confidence levels are determined based on the bin weights and on the confidence levels,
a prediction generator communicatively coupled to the distribution adapter, the prediction generator to automatically predict a length of stay of a target admission based on the weighted confidence levels, and
a user interface device communicatively coupled to the resource management apparatus, the user interface device to output the predicted length of stay.

2. The system of claim 1, wherein the distribution adapter is to determine, for each data bin, a fraction of total elements that belong to the data bin, and compute a product between the fraction and the confidence level assigned to the data bin.

3. The system of claim 1, wherein the confidence differentiator is to determine, for each data bin, an average similarity factor based on the similarity data, and determine, for each data bin, a confidence level based on the average similarity factor.

4. The system of claim 1, wherein the resource management apparatus further includes:
a readmission monitor to detect that the target admission is a real-time readmission of a target patient, and
a diagnosis analyzer communicatively coupled to the readmission monitor, the diagnosis analyzer to identify one or more common diagnoses associated with the real-time readmission, wherein the one or more common diagnoses indicate diagnoses in the target admission that are shared with one or more recent admissions of the target patient.

5. The system of claim 4, wherein the readmission monitor is to compute a difference between an admission time of the target admission and an admission time of a previous admission associated with the target patient, and detect that the difference does not exceed a threshold.

6. The system of claim 4, wherein the resource management apparatus further includes:
a diagnosis reporter to determine a ratio between the one or more common diagnoses and total diagnoses associated with the real-time readmission; and
a readmission rate reporter to update a percentage of total readmissions based on the one or more common diagnoses.

7. An apparatus comprising:
a confidence differentiator to assign confidence levels to a plurality of data bins containing similarity data and length of stay data, wherein the similarity data and the length of stay data both correspond to a plurality of previous admissions of other patients, wherein a first confidence level is assigned to a first data bin that contains similarity data associated within a first length of stay range, and wherein a second confidence level is assigned to a second data bin that contains similarity data within a second length of stay, wherein the second confidence level is different from the first confidence level, and wherein the second length of stay range is different from the first length of stay range;
a distribution adapter communicatively coupled to the confidence differentiator, the distribution adapter to weigh the confidence levels based on a distribution metric that assigns a first weight to a first data region having a first density and assigns a second higher weight to a second data region having a second higher density, wherein each bin weight represents the relative density of one of the plurality of data bins and the bin weights sum to a value of one, and wherein the weighted confidence levels are determined based on the bin weights and on the confidence levels; and
a prediction generator communicatively coupled to the distribution adapter, the prediction generator to automatically predict a length of stay of a target admission based on the weighted confidence levels.

8. The apparatus of claim 7, wherein the distribution adapter is to determine, for each data bin, a fraction of total elements that belong to the data bin, and compute a product between the fraction and the confidence level assigned to the data bin.

9. The apparatus of claim 7, wherein the confidence differentiator is to determine, for each data bin, an average similarity factor based on the similarity data, and determine, for each data bin, a confidence level based on the average similarity factor.

10. The apparatus of claim 7, further including:
a readmission monitor to detect that the target admission is a real-time readmission of a target patient; and
a diagnosis analyzer communicatively coupled to the readmission monitor, the diagnosis analyzer to identify one or more common diagnoses associated with the real-time readmission, wherein the one or more common diagnoses indicate diagnoses in the target admission that are shared with one or more recent admissions of the target patient.

11. The apparatus of claim 10, wherein the readmission monitor is to compute a difference between an admission time of the target admission and an admission time of a previous admission associated with the target patient, and detect that the difference does not exceed a threshold.

12. The apparatus of claim 10, further including:
a diagnosis reporter to determine a ratio between the one or more common diagnoses and total diagnoses associated with the real-time readmission; and
a readmission rate reporter to update a percentage of total readmissions based on the one or more common diagnoses.

13. A method comprising:
assigning confidence levels to a plurality of data bins containing similarity data and length of stay data, wherein the similarity data and the length of stay data both correspond to a plurality of previous admissions of other patients, wherein a first confidence level is assigned to a first data bin that contains similarity data associated within a first length of stay range, and wherein a second confidence level is assigned to a second data bin that contains similarity data within a second length of stay, wherein the second confidence level is different from the first confidence level, and wherein the second length of stay range is different from the first length of stay range;
weighing the confidence levels based on a distribution metric that assigns a first weight to a first data region having a first density and assigns a second higher weight to a second data region having a second higher density, wherein each bin weight represents the relative density of one of the plurality of data bins and the bin weights sum to a value of one, and wherein the weighted confidence levels are determined based on the bin weights and on the confidence levels; and
automatically predicting a length of stay of a target admission based on the weighted confidence levels.

14. The method of claim 13, wherein weighing the confidence levels includes:
determining, for each data bin, a fraction of total elements that belong to the data bin; and
computing a product between the fraction and the confidence level assigned to the data bin.

15. The method of claim 13, wherein assigning the confidence levels includes:
determining, for each data bin, an average similarity factor based on the similarity data; and
determining, for each data bin, a confidence level based on the average similarity factor.

16. The method of claim 13, further including:
detecting that the target admission is a real-time readmission of a target patient; and
identifying one or more common diagnoses associated with the real-time readmission, wherein the one or more common diagnoses indicate diagnoses in the target admission that are shared with one or more recent admissions of the target patient.

17. The method of claim 16, wherein detecting that the target admission is a real-time readmission includes:
computing a difference between an admission time of the target admission and an admission time of a previous admission associated with the target patient; and
detecting that the difference does not exceed a threshold.

18. The method of claim 16, further including:
determining a ratio between the one or more common diagnoses and total diagnoses associated with the real-time readmission; and
updating a percentage of total readmissions based on the one or more common diagnoses.

19. At least one non-transitory computer readable storage medium comprising a set of instructions, which when executed by a computing system, cause the computing system to:
assign confidence levels to a plurality of data bins containing similarity data and length of stay data, wherein the similarity data and the length of stay data both correspond to a plurality of previous admissions of other patients, wherein a first confidence level is assigned to a first data bin that contains similarity data associated within a first length of stay range, and wherein a second confidence level is assigned to a second data bin that contains similarity data within a second length of stay, wherein the second confidence level is different from the first confidence level, and wherein the second length of stay range is different from the first length of stay range;
weigh the confidence levels based on a distribution metric that assigns a first weight to a first data region having a first density and assigns a second higher weight to a second data region having a second higher density, wherein each bin weight represents the relative density of one of the plurality of data bins and the bin weights sum to a value of one, and wherein the weighted confidence levels are determined based on the bin weights and on the confidence levels; and
automatically predict a length of stay of a target admission based on the weighted confidence levels.

20. The at least one non-transitory computer readable storage medium of claim 19, wherein the instructions, when executed, cause the computing system to:
  determine, for each data bin, a fraction of total elements that belong to the data bin; and
  compute a product between the fraction and the confidence level assigned to the data bin to weigh the confidence levels.

21. The at least one non-transitory computer readable storage medium of claim 19, wherein the instructions, when executed, cause the computing system to:
  determine, for each data bin, an average similarity factor based on the similarity data; and
  determine, for each data bin, a confidence level based on the average similarity factor to assign the confidence levels.

22. The at least one non-transitory computer readable storage medium of claim 19, wherein the instructions, when executed, cause the computing system to:
  detect that the target admission is a real-time readmission of a target patient; and
  identify one or more common diagnoses associated with the real-time readmission, wherein the one or more common diagnoses indicate diagnoses in the target admission that are shared with one or more recent admissions of the target patient.

23. The at least one non-transitory computer readable storage medium of claim 22, wherein the instructions, when executed, cause the computing system to:
  compute a difference between an admission time of the target admission and an admission time of a previous admission associated with the target patient; and
  detect that the difference does not exceed a threshold to detect that the target admission is a real-time readmission.

24. The at least one non-transitory computer readable storage medium of claim 22, wherein the instructions, when executed, cause the computing system to:
  determine a ratio between the one or more common diagnoses and total diagnoses associated with the real-time readmission; and
  update a percentage of total readmissions based on the one or more common diagnoses.

* * * * *